United States Patent
Robinson (10) Patent No.: US 8,660,237 B2
(45) Date of Patent: Feb. 25, 2014

(54) APPARATUS AND METHOD FOR VIEWING AN OBJECT

(75) Inventor: Max Robinson, Shincliffe (GB)

(73) Assignee: Kromek Limited, Sedgefield, County Durham (GB)

( * ) Notice: Subject to any disclaimer, the term of this patent is extended or adjusted under 35 U.S.C. 154(b) by 42 days.

(21) Appl. No.: 13/148,621

(22) PCT Filed: Jan. 26, 2010

(86) PCT No.: PCT/GB2010/050108
§ 371 (c)(1),
(2), (4) Date: Sep. 16, 2011

(87) PCT Pub. No.: WO2010/092368
PCT Pub. Date: Aug. 19, 2010

(65) Prior Publication Data
US 2012/0004513 A1    Jan. 5, 2012

(30) Foreign Application Priority Data
Feb. 10, 2009    (GB) .................................. 0902138.7

(51) Int. Cl.
*G03B 42/02* (2006.01)
*A61B 6/02* (2006.01)

(52) U.S. Cl.
USPC ................................. 378/41; 378/57; 600/407

(58) Field of Classification Search
None
See application file for complete search history.

(56) References Cited

U.S. PATENT DOCUMENTS

| | | | | | |
|---|---|---|---|---|---|
| 4,672,649 | A | * | 6/1987 | Rutt | 378/10 |
| 4,696,022 | A | * | 9/1987 | Sashin et al. | 378/41 |
| 5,644,324 | A | * | 7/1997 | Maguire, Jr. | 345/9 |
| 5,745,544 | A | * | 4/1998 | Mazess | 378/56 |
| 6,018,562 | A | * | 1/2000 | Willson | 378/9 |
| 6,081,582 | A | * | 6/2000 | Mazess et al. | 378/146 |
| 6,256,372 | B1 | * | 7/2001 | Aufrichtig et al. | 378/41 |
| 6,862,364 | B1 | * | 3/2005 | Berestov | 382/132 |
| 6,944,263 | B2 | * | 9/2005 | Xiao et al. | 378/41 |
| 2008/0298538 | A1 | | 12/2008 | Wen et al. | |

FOREIGN PATENT DOCUMENTS

| | | |
|---|---|---|
| EP | 0 261 984 A2 | 9/1987 |
| EP | 0 261 984 A3 | 9/1987 |
| EP | 0 610 084 A3 | 8/1994 |
| EP | 0 610 084 B1 | 4/1998 |

(Continued)

OTHER PUBLICATIONS

JP Office Action, Nov. 12, 2013, 2011-548779, 7 pages (including translation and identifying the pertinence of each reference).

*Primary Examiner* — Jacqueline Cheng
(74) *Attorney, Agent, or Firm* — Drinker Biddle & Reath LLP (57) ABSTRACT

An apparatus and method for generating and displaying an image of an object is described and includes a radiation source and a series of at least two linear detectors capable of detecting incident radiation after transmission through an object to define a scanning zone there between. The object is moved relative to and through the scanning zone in successive passes along at least two linear directions at an angle to each other. An image generation apparatus generates for each successive pass at least a first image from the first linear detector, a second image from the second linear detector, and a third image. An image display is adapted successively to display at least the first, second and third images and display the monocular movement parallax between the images. Each image is processed before display to reduce distortion attributable to beam spreading in a direction perpendicular to a scan direction.

27 Claims, 5 Drawing Sheets

(56) References Cited

FOREIGN PATENT DOCUMENTS

| | | |
|---|---|---|
| GB | 2 329 817 | 3/1999 |
| GB | 2 360 685 | 9/2001 |
| JP | 2008298762 A | 12/2008 |
| WO | WO 2008/119967 | 10/2008 |
| WO | WO 2008/119967 A3 | 10/2008 |

* cited by examiner

APPARATUS AND METHOD FOR VIEWING AN OBJECT

FIELD OF THE INVENTION

This invention relates to an apparatus and method for imaging an object in three-dimensional space using incident high energy radiation scanning, for example with x-rays.

BACKGROUND

The invention in particular relates to an apparatus and method operating on the line-scan principle, in which three dimensional objects are caused to move through a scanning zone and imaging information collected. This principle is widely employed for example without limitation in the security industry, to scan objects where it is desirable to gain information about their internal contents, and in medical imaging, imaging for quality control purposes or the purposes of determining the integrity of the structure, or the like.

Imaging apparatus which employs the line-scan principle is well known. Typically, such apparatus will consist of an x-ray source, the beam of which may be collimated into a curtain, usually referred to as a "curtain beam", and is then detected by a linear array detector for example comprising a linear photodiode array. Image information is obtained by having the object of interest move linearly for example at right angles with respect to the beam and storing successive scans of x-ray transmission information derived from the linear array from which a complete image frame can be compiled.

If the object being scanned is heterogeneously transmissive of x-ray radiation, and for example consists of or contains multiple smaller objects and/or components of dissimilar materials, it can be possible to build up an image of the object, and in a particular case of the contents or components. The image may then be displayed on a viewing screen. This image can be useful for example in relation to the possible applications outlined above. In particular, it can be useful in determining the contents of a container or the internal structure of an object or body.

Even so, the image generated by such an x-ray apparatus is limited. At best it constitutes a two dimensional shadowgraph of the object being imaged. This can make it difficult to interpret.

European Patent No. 0610084 describes a method of creating a "2.5D" solid model picture for viewing. A stereoscopic pair of x-ray images is obtained using two diverging curtain beams derived from an x-ray source. These are separated into conjugate slices and the 2.5D image built up from the resulting slice information.

The resultant image is not strictly a three dimensional image (although it is often so referred to) since it is presented on a two dimensional screen rather than by means of full stereoscopic apparatus. Such a 2.5D representation in fact contains psychological cues to depth such as linear perspective, interposition, shading and shadowing rather than the full physiological depth cue known as binocular parallax or stereoscopy which is required for a full three dimensional image.

UK Patent Nos. 2329817 and 2360685 are examples of methods and systems which can be used to produce full stereoscopic image pairs. They derive ultimately from principles set out in European Patent No 0261984. In particular they are subject to the condition set out at column 4 lines 31 to 48 therein which imposes considerable constraints on detector and source beam geometry. Although stereoscopic imaging can be a relatively powerful technique, exploiting full physiological cues in relation to depth information, and thus offering the potential for a user of the x-ray apparatus to identify objects or components much more readily and clearly, it can be complex in practical operation. To exploit the stereoscopic effect, it is necessary for the observer to receive different images at each eye simultaneously. This will necessitate the use of special apparatus. Moreover, a full stereoscopic technique requires precise control of the image collection process having regard to the conditions identified above. If the stereoscopic pair is to be effective, the respective images must be collected with a parallax that closely approximates to that which would be tolerated by the observer's eyes. For these reasons, full stereoscopic imaging has not gained wide acceptance for scanning machines of this type.

Some of these problems are mitigated by PCT publication WO2008/119967 in which the line-scan principle is used to generate successive images as relative movement is effected along a single linear axis between an object and a source/detector arrangement so as to display the monocular movement parallax between such successive images and offer some further three-dimensional cues.

The line-scan x-ray technique might find application in relation to imaging for medical or other investigative examination purposes, quality control etc where it is desirable to view a multi-component target object. A better resolution of the exact shape and location of components of objects in three-dimensional space would be a considerable improvement on present techniques, especially if composition could also better be characterised.

SUMMARY OF THE INVENTION

It is an object of the present invention to mitigate some or all of the above disadvantages of prior art line scanning systems.

Therefore, according to one aspect of the invention there is provided an apparatus for generating and displaying an image of an object comprising:

a radiation source and a series of at least two but preferably three or more linear detectors capable of detecting incident radiation spaced therefrom to define a scanning zone therebetween;

means to cause an object to move relative to and through the scanning zone in use in successive passes along at least two linear directions at an angle to each other;

an image generation apparatus to generate for each successive pass at least a first image from the output of a first linear detector, a second image from the output of a second linear detector, and a third image;

an image processing apparatus adapted to process collected image data from the output of the linear detectors in such manner as to reduce distortion attributable to beam spreading in a direction perpendicular to a scan direction;

an image display adapted successively to display at least the first, second and third such images and thus display the monocular movement parallax between the images.

By analogy, in accordance with a further aspect of the invention there is provided a method of obtaining an image of an object comprising the steps of:

providing a radiation source and a series of at least two but preferably three or more linear detectors capable of detecting incident radiation spaced therefrom to define a scanning zone therebetween;

causing an object to move relative to and through the scanning zone in successive passes in at least two linear directions at an angle to each other; and thereby generating for each successive pass at least a first image from the output of a first linear detector at least a second image from the output of a second linear detector; and at least one third image;

processing collected image data for each image in such manner as to reduce distortion attributable to beam spreading in a direction perpendicular to a scan direction;

displaying at least such first, second and third images successively and thus displaying the monocular movement parallax between the images.

Thus, in accordance with the apparatus and method of the first and second aspects of the invention successive images are generated as relative movement is effected between an object and a source/detector arrangement, from the radiation incident at the detector arrangement as radiation interaction occurs between radiation from the source and the object moving through the scanning zone, and especially from radiation incident at the detector arrangement after transmission through the object. The images are thus successive radiographs, and especially successive transmission radiographs.

Suitable means are provided to effect relative movement of object and scanning zone, for example comprising an object handler and/or scanning arm. It may be convenient for an object to be moved, for example by a suitable object handler or conveyor, through a static scanning zone, but it will be appreciated that it is often preferable to have the object remain static and to translate the detector and source to create the relative movement. A suitable scanning arm may comprise a moveable source and/or detector array.

The invention is distinctly characterised in that multiple passes are made along a plurality of axes, and a set of images exhibiting monocular movement parallax is collected on each pass. For example, a scanning arm is used to effect relative movement between an object and a source/detector arrangement, for example in that the scanning arm carries a detector array and source. The detector array and source may be moved together over a stationary object in a linear pass direction. After a pass in a first direction the scanning arm may be repositioned, and for example rotated about an axis equivalent to a notional central point of the object to be viewed, and another scanning pass could be made in a second direction. The process could be repeated in further scanning pass directions. On each such pass another set of images potentially displaying monocular movement parallax would be captured.

Images produced by using line scan detectors with suitable radiation sources exhibit some unique properties. Because of the point source typically used, a collimated curtain beam designed to be incident upon a linear array will exhibit familiar point source distortion along its length which is characteristic of radiographs in general. However, in the direction of movement no such distortion will exist. This is of considerable significance since it makes possible introduction of powerful depth cues into radiographs such as those attributable to binocular stereopsis or monocular movement parallax.

As has been noted above, the conditions which must be fulfilled for stereoscopic images to be produced are quite rigid and tend to require specialist viewing arrangements. However, monocular movement parallax images do not suffer from such constraints. Thus, useful third dimensional cues can be obtained for a given series of images.

In accordance with the invention, multiple passes are made along a plurality of axes, and a set of images exhibiting monocular movement parallax is collected on each pass. Although each set of images is undistorted in a movement direction for the reasons set out above, the geometry of the linear detector and the effect of beam spreading will produce distortion via a vignetting effect in any area radiograph in a direction perpendicular to the scanning direction. This might not be a major problem where a series of images is generated in a single scan direction, since all such images in the series are distorted in a like sense, and this does not unduly affect comprehensibility. It is more of a problem where images are generated along multiple passes, in that distortion attributable to vignetting will be in multiple directions.

Accordingly, the method of the invention is distinctly characterised in that in an additional step prior to image display each image for each successive pass is processed in such manner as to produce an image with reduced distortion attributable to beam spreading in a direction perpendicular to a scan direction, and in particular to produce an image with an aspect ratio (that is, a ratio of apparent length in a scan direction and apparent length perpendicular to the scan direction) which approximates more closely to reality.

There are two principal ways in which the image aspect ratio of an image for display can be controlled. First, a scanning rate may be controlled and varied in functional manner to induce a distortion in a scanning direction which tends to correspond with a distortion attributable to beam spreading in a direction perpendicular to a scanning direction. In this way, the collected intensity data is itself inherently adjusted to approximate in spatial coordinates to a real aspect ratio and any image generated therefrom is similarly inherently adjusted. Second, incident intensity data may be collected including beam spreading effects, and a suitable numerical analysis methodology may be applied to the collected data to compensate for the distortion and to produce an image with an aspect ratio substantially approximating to reality. An image analysis by numerical methodology for example using a suitable image analysis method is particularly preferred. For example the method may comprise applying a scaling factor to the measured position in a direction perpendicular to a scan direction of collected data to generate a notional position that is corrected for beam spreading or vignetting in a direction perpendicular to a scan direction. Combinations of these two techniques may be applied.

Consequently it follows by analogy in accordance with the first aspect of the invention that the apparatus further includes an image processing apparatus to process collected image data from the output of the linear detectors in such manner as to reduce distortion attributable to beam spreading, and in particular to produce an image with an aspect ratio that approximates to reality. For example the apparatus includes a numerical correction module to apply a numerical image analysis to collected data to compensate for the distortion attributable to beam spreading or vignetting in a direction perpendicular to a scan direction, for example to apply a scaling factor to collected data to correct for beam spreading or vignetting in a direction perpendicular to a scan direction.

Collecting images in accordance with the invention across plural axes and processing these to correct for vignetting effects means that the reduction of distortion along the direction of the linear array can be exploited for each pass, and the resultant multiple series of parallax images used in practice to generate images with three dimensional cues along a plurality of axes with the detrimental effect on comprehensibility of such images attributable to distortion from vignetting reduced or eliminated.

For example, if a medical application is considered, when viewing a complex fracture of an arm for instance, it would be advantageous to view a rotational series of images along the length of the arm as well as one at 90 degrees. Other image series at angles in between these 90 degree extremes could be added to the data set. The apparatus and method in accordance with the invention provides a powerful tool to deliver these cues from a simple line scan principle, especially when corrected for distortion perpendicular to the scan direction.

For each pass, at least three images are generated from at least one spaced pair (and preferably a series of at least three) linear detectors. Although a plurality of images is generated, the images are not collected and displayed as paired images with the intention of providing a stereoscopic effect. Rather, the invention exploits the monocular movement parallax between the successive images in each series.

Monocular movement parallax alone can give some effective physiological cues in relation to objects located in three-dimensional space, in particular if a successive multiple series of images is used, although the effect will be present for any pair of images. It has a number of advantages of simplicity over a full stereoscopic system.

In particular, the images are displayed successively as individual two-dimensional images, and require no special apparatus. The system exploits a monocular parallax. It is not necessary simultaneously to generate different images for each eye of a user as would be the case for stereoscopic viewing. A binocular or other complex stereoscopic viewing apparatus is not required. A simple monocular display is sufficient. Moreover, the relatively strict control of image production which is necessary to exploit binocular parallax effectively does not apply. For example for an effective binocular parallax pair of images, the images need to be generated in such a way that the parallax between them closely matches that which can be tolerated by a human observer. By contrast, an effective monocular parallax illusion of movement in three dimensions can be produced by a much greater range of successive images. It is not necessary to comply with the narrow conditions for beam geometry that apply to stereoscopic imaging.

The system and method in accordance with the first and second aspects of the invention are thus potentially simpler in many practical circumstances than a binocular method and apparatus, and, significantly, the invention tends to lend itself more closely to application with limited modification to existing apparatus and techniques.

The refinement of the technique to generate multiple series of monocular movement parallax images by performing successive scans comprising successive passes of relative movement between a source/detector arrangement and an object in a plurality of directions at an angle to each other enhances this effect by providing the possibility of, in effect, rotating the resultant views. This is particularly effective when each series is corrected for vignetting as above described.

The key to the invention relates to scanning in at least two different directions and making use of the additional information that accrues from performing at least two such passes. If the images are corrected to remove distortion then the images from the multiple passes can be combined, which give the ability to manipulate the data to change the object axis around which the object is being "viewed" in a resultant image. By presenting such images successively in suitable order, an animated "moving" image representation may be generated of an object which is manipulatable under viewer control with three dimensional degrees of freedom. In the preferred case, at least three passes are successively performed respectively along at least three linear directions. Preferably, at least three directions intersect at a single common point of intersection, which represents a notional imaging centre of an object.

The monocular movement parallax effect is present in theory in just a pair of images, and visual cues in a third dimension which enable a user to resolve objects, and in particular individual contents and/or components thereof, being scanned can be obtained from such a simple pair of images for a given pass. However, the effect is enhanced, and in particular a more effective impression of movement in three dimensions can be obtained, if a series of more than two successive images is generated and displayed for each pass. In accordance with the invention, at least three images are generated for each pass. More preferably at least six images are generated for each pass.

There are two ways in which additional images can be generated. First, there may be provided a laterally spaced series of more than two linear detectors, for example at least three detectors, and more preferably at least five detectors. The output of each such detector may then be used singly to generate an image representative of data collected at the detector.

Where a plural series of laterally spaced linear detectors is provided, the space in between them is preferably generally constant, for example in that each pair of adjacent linear detectors in the series is substantially equally laterally spaced and/or at a substantially equal angular spacing relative to the source.

The linear detectors making up the laterally spaced series are preferably generally parallel. They may be disposed in a common plane or along a common arc. Each linear detector may be of any suitable configuration, for example of a conventional simple or folded configuration.

Preferably the linear detectors making up the laterally spaced series are arranged such that the distance between them changes in order to maintain a constant angular separation between each array. This is of critical importance for L-shaped detectors which are commonly found in many scanning industries. This innovation is also of critical importance when the source of the radiation is not positioned at the central point of each array.

Preferably the apparatus comprises alignment means to allow for precise alignment of each linear detector as above described.

Preferably the apparatus comprises means to deliver plural beams, preferably from a single radiation source. For example a beam is directed at each linear detector. Preferably the means to deliver plural beams allows a user to select a desired number of beams to correspond to the number of detectors in a plural array. Conveniently the apparatus comprises a collimator adapted to allow a user to select two to five beams from a single source.

Additionally or alternatively, further images may be generated by interpolation of pairs of images collected from adjacent linear detectors. Thus, in accordance with a preferred embodiment of the invention, the method additionally comprises generating at least one intermediate image from at least one adjacent pair, and where applicable preferably generating at least one intermediate image from a plurality of adjacent pairs and for example each adjacent pair, of linear detectors, by processing the output of the or each said pair of detectors and generating an image representative of an output intermediate between the two said detected outputs.

The apparatus of the invention preferably includes an intermediate image generator comprising a means having this functionality.

Where a single intermediate image is generated between an adjacent pair of detected images, the intermediate image preferably extrapolates image points on the intermediate image to a mid-point between equivalent image points on the two detected images. Where a plurality of intermediate images is provided between a pair of detected images these are preferably based on a similar, evenly spaced extrapolation. Further preferably, the relative spacing of detectors and the configuration of intermediate image generation is such that all images are generated with approximately the same relative movement spacing. For example detectors are evenly spaced and the same number of intermediate images is generated between each pair of a plural array.

In accordance with the foregoing, either or both approaches is used to generate a series of images of an object in a scanning zone in what amounts, in effect, to different positions. In the first approach, a plurality of spaced detectors produce a corresponding plurality of direct images. In the second approach, actual data from adjacent linear detectors is used to generate an indirect image intermediate to the direct images, and thus representative of an intermediate object position.

Either or both methods may be used to generate a successive series of images from which, by means of the monocular movement parallax between each pair of successive images, information about a third dimension, and in particular an impression of movement through a third dimension, can be obtained. A relatively small number of images is required to produce an effective animation-like movement in three dimensions by a user observing a simple two-dimensional screen.

In accordance with the invention at least three images are generated in each series (i.e. for each pass). It will be appreciated in accordance with the foregoing that a third image requires either the use of a third detector to generate a third direct image or the use of the interpolation method to generate a third, indirect image from the output of a single pair of detectors. In practice both effects may be exploited together and a larger plurality of images might be preferred, for example at least three detectors generating at least five images, directly and by the interpolation method. However, a large number of linear detectors is not necessarily desirable and may require more complex apparatus. For example it might be desirable to provide five or fewer but to generate seven or more images for a given pass in a given direction.

In a preferred embodiment therefore an intermediate image generator is provided as above, configured such that seven or more images in total are generated for each pass from five or fewer detectors. In this preferred embodiment an apparatus comprises a laterally spaced series of no more than five linear detectors, a direct image generation apparatus configured to generate an image from the output of each linear detector and an intermediate image generation apparatus configured to generate at least one intermediate image from each adjacent pair of linear detectors and adapted such that at least seven images are generated in total. In this preferred embodiment the method comprises generating a direct image from the output of each linear detector; generating at least one intermediate image from the or each adjacent pair of linear detectors, by processing the output of the or each said pair of detectors and generating an image representative of an output intermediate between the two said detector outputs; such that at least seven direct and intermediate images are generated in total.

Sufficient intermediate images are generated to create at least seven images in total (that is, when direct images collected from the direct detected output of each detector and intermediate images generated by interpolation are summed). Where only two or three detectors are used additional images are created by synthesising more than one virtually spaced intermediate images between sufficient pair of detectors to result in the required number of images. The intermediate image generator is then configured to generate two or more intermediate images from at least one adjacent pair which show a gradual transition between the images produced by each adjacent pair by processing the output of the or each said pair of detectors and generating image representatives of a transition between the two said detected outputs.

Thus the embodiment generates at least seven images for optimum resolution of the parallax effect by a human viewer, but in all cases with five or fewer linear detector arrays. Sufficient visual information is generated from a simplified apparatus.

It has been noted that the invention, by scanning in at least two different directions and preferably correcting image data to remove distortion, can allow images from the multiple passes to be combined, which give the ability to change the object axis around which the object is viewed. The principle of intermediate image generation outlined above in relation to a given pass in a given direction may also be employed for the generation of intermediate images as the object is rotated between different real imaging axes.

That is to say, one or more further images may be generated by interpolation of pairs of images collected from a pair of first and second pass directions and presented successively as the object is presented with an imaging direction rotated between the first and second pass directions to create a smoother transition in the presented image. Thus, in accordance with a preferred embodiment of the invention, the method additionally comprises generating at least one intermediate image from at least one pair of image positions respectively generated at first and second pass directions, by processing the detected output for each such image position and generating an image representative of an output intermediate between the two said detected outputs.

Similar principles to those outlined above may be applied to generate an intermediate image between two real image directions. For example, where a single intermediate image is generated between a pair of detected images in two real image directions, the intermediate image preferably extrapolates image points on the intermediate image to a mid-point between equivalent image points on the two detected images. Where a plurality of intermediate images is provided between a pair of detected images these are preferably based on a similar, evenly spaced extrapolation.

The apparatus of the invention preferably includes an intermediate image generator comprising a means having this functionality.

Conveniently, a single image generator, for example comprising suitable software, is provided with a capability of generating, from pairs of data for real imaging positions, intermediate images for virtual image positions between adjacent detectors and/or intermediate images for virtual image positions between pairs of scan axes in the manner above described. The resultant dataset of collected and virtual images allows fuller manipulation of the object in three degrees of freedom, and enhances the resultant information content and value of any image display.

The parallax effect may be supplemented in accordance with a possible embodiment of the invention by a second effect that assists in resolution of different objects, components or parts of an image by presenting spectroscopic information differentially in the image (and thus presenting information having a relationship to composition differentially).

Prior art conventional scintillator-semiconductor detectors do not give any real spectroscopic information about the spectrum of transmitted radiation. These simple detectors merely detect the presence or otherwise of transmitted x-rays. Even the dual energy detectors ultimately operate on the same principle, although they detect the presence or otherwise of x-rays within two distinct bands of the spectrum.

However, in accordance with a preferred embodiment of the invention at least some of the linear detectors in the series comprise detectors that can generate spectroscopically resolved information about the transmitted radiation across at least part of the source spectrum. That is, the detector exhibits a spectroscopically variable response across at least a part of the source spectrum allowing spectroscopic information to be retrieved and allowing intensity information to be detected at a plurality of differentiated energy bands across at least part of, and preferably a major part of, the spectrum of the source. Intensity information is resolved into a plurality of differentiated energy bands in the sense that it is differentiated simultaneously into plural separate energy bands across the spectrum of the source. The detector system is capable of detecting and collecting spectroscopically resolvable information about incident radiation in the sense that it is adapted to differentiate incident radiation simultaneously into plural separate energy bands across the spectrum of the source.

Proper resolution of spectroscopic information confers two advantages. It offers the potential directly to characterise the composition of different components or objects, or parts of the image, and by distinguishing between objects, components or parts of different composition, for example by representing them differently (such as in different colours) in the resultant image, it assists in resolution of different objects, components or parts of the image.

In accordance with the preferred embodiment, spectroscopic resolution of transmitted radiation obtained from the output of each such linear detector is represented in the generated image. For example, spectroscopic differentiation in the collected data is represented in the image as differentiated colour, shading or marking. For example, a functional mapping is created between the spectroscopic information collected by the detector and the visual spectrum, and a coloured image display derived according to this functional relationship. Alternatively, a banded mapping is used in that the spectrum is divided into a plurality of bands, for example between four and eight bands, and different colours are used to represent each such band in the displayed image. The apparatus conveniently includes suitable image processing means to effect this mapping. Also as previously mentioned, images can be displayed either as single energy bands or as combinations of energy bands.

It is necessary that the detector system is enabled to detect radiation in a manner which is spectroscopically resolvable by the data processing apparatus. Preferably, a linear detector system in accordance with the invention, or some or all discrete detector elements making up a multi-element detector system in accordance with the invention, may be inherently adapted to produce spectroscopic resolution in that it exhibits a direct spectroscopic response. In particular a system or element is fabricated from a material selected to exhibit inherently as a direct material property a direct variable electrical and for example photoelectric response to different parts of the spectrum of the source. For example, the detector system or element comprises a wide direct bandgap semiconductor material. For example, the detector system or element comprises a semiconductor material or materials preferably formed as a bulk crystal, and for example as a bulk single crystal (where bulk crystal in this context indicates a thickness of at least 500 μm, and preferably of at least 1 mm). The materials making up the semiconductor are preferably selected from cadmium telluride, cadmium zinc telluride (CZT), cadmium manganese telluride (CMT), germanium, lanthanum bromide, thorium bromide. Group II-VI semiconductors, and especially those listed, are particularly preferred in this regard. The materials making up the semiconductor are preferably selected from cadmium telluride, cadmium zinc telluride (CZT), cadmium manganese telluride (CMT) and alloys thereof, and for example comprise crystalline $Cd_{1-(a+b)}Mn_aZn_b Te$ where a+b<1 and a and/or b may be zero.

Combination of these and any other such materials may be considered which give spectroscopic detection rather than merely detecting amplitude of incident radiation monochromatically.

The basic geometry comprising at least two linear array detectors in serial array, and preferably a plurality of the same, to allow the generation of multiple images and to view these as an animated sequence is fundamental to the invention in providing an enhanced ability to interpret the shape and form of the object.

However, the greatly improved materials identification capability conferred by using spectroscopic linear detectors enhances both the ability inherently to identify composition of objects and the resolvability of different objects in an image via a number of steps which could be additive and reinforcing.

In particular for example spectroscopic detectors can be operated in an energy selective manner, giving rise to the ability to present an image resolved into a significantly increased number of energy bands compared with the two that are available from standard prior art dual energy detectors. This information can be used to provide a much higher degree of material identification than is currently possible and also, by separately identifying objects of different compositions within a composite image, to improve resolvability of such objects.

Conveniently, the successive images are displayed under observer control, for example in that control means are provided to enable a user to display successive images under control, and for example at a chosen speed and/or in a forward and reverse order on the image display means, so as to create an effective manipulation of third dimensional cues from each image series and from display of successive series. For example this allows a user to display successive images at variable speeds in order to enable a smooth transition for the human observer between each image and/or to run the images in a forward and reverse order. In accordance with the method of the invention the successive images are thus displayed at custom definable refresh rates and directions under observer control to facilitate interpretation.

The apparatus of the invention is particularly suited to applications where it is preferable to have an object under test remain static and to translate the detector and source to create the relative movement. The apparatus may conveniently comprise at least detector and source, and preferably other components, compactly associated together in a portable means for scanning of objects in situ on location.

The apparatus and method of the invention are particularly suited to the scanning of parts of the human or animal body for various purposes, whether medical/veterinary or otherwise, including the observation of its internal operation whether for diagnostic or other purposes and the observation of abnormalities or injury. The preferred case, where the source/detector arrangement is mobile in particularly suited to the examination of parts of the body for injury, for example in situ where injury has occurred or locally thereto at a field casualty location.

In a preferred case, the method comprises a method of obtaining imaging data from a part of the human or animal body, whether for diagnostic or other purposes, and comprises scanning the part of the body as an object in the manner above described. In a particular preferred case, the method comprises a method of diagnosis of a disorder of the human or animal body, such as a trauma injury, including the step of imaging the body as above, and the further step of evaluating the image to identify a disorder state such as a trauma injury. This is particularly applicable in the preferred case where an energy selective analysis is used to generate information about composition. The apparatus is conveniently adapted to facilitate such use.

The display means is conveniently a simple two dimensional display screen, for example a conventional video display screen (which term is intended to encompass any direct display or projection system exploiting any cathode ray tube, plasma display, liquid crystal display, liquid crystal on silicon display, light emitting diode display or like technology). It is a particular advantage that the method can be envisaged for use with, and the apparatus for the invention incorporated into, the standard display screens of comparable existing systems for example in the security or medical imaging fields.

The radiation source preferably comprises a source to deliver high-energy radiation such as ionising radiation, for example high-energy electromagnetic radiation such as x-rays and/or gamma rays, or subatomic particle radiation, and the detection system is adapted correspondingly to detect radiation in this spectrum. The radiation source for example is a broadband source such as a broadband x-ray or gamma-ray source capable of producing broad spectrum emission over a wide range of energies.

The radiation source is preferably a curtain beam source as will be familiar from conventional line scan apparatus. The source may comprise a single primary source adapted to generate a series of beams such as curtain beams aligned to be incident upon each linear detector in the laterally spaced serial array at a suitable angular separation, for example by a suitable beam splitting apparatus. Alternatively, multiple sources may be provided each generating a beam such as a curtain beam incident upon a linear detector in the serial array. The source may comprise a source combining both of the foregoing principles.

Each linear detector in the laterally spaced series is a detector for the detection of transmitted radiation. For example, each detector is adapted to generate an electrical impulse in response to transmitted radiation, thus enabling data to be collected from which an image can be constructed as an object is caused to move through the scanning zone. Each detector conveniently exhibits a photoelectric response and may for example comprise a linear array of photodiode cells.

BRIEF DESCRIPTION OF THE DRAWINGS

The invention will now be described by way of example, with reference to the accompanying drawings in which.

DESCRIPTION OF THE PREFERRED EMBODIMENTS

Figure 1A:
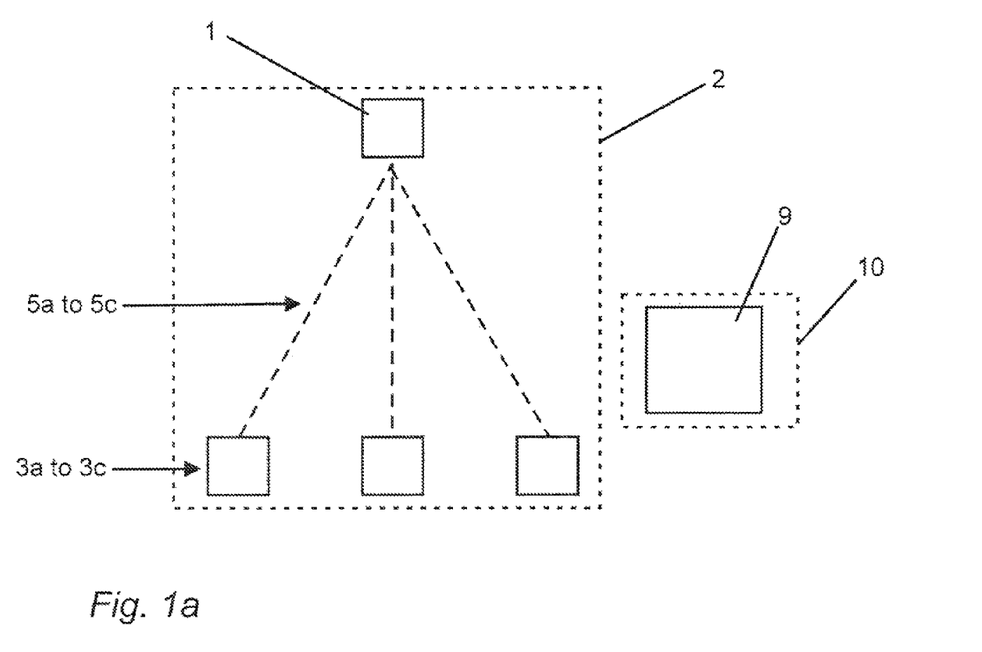
FIG. 1 is a representation of a single image series generated by the principles of the invention.

Referring to FIG. 1a, a suitable x-ray source 1 is used to direct x-rays via a scanning zone in the direction of three linear array detectors 3a to 3c.

In the embodiment, the linear array detectors 3a to 3c comprise material capable of spectroscopic resolution of incident x-rays, and in the specific example comprise cadmium telluride although the skilled person will appreciate that other material selections may be appropriate. To exploit this spectral resolution, the x-ray source emits x-ray across a broad energy spectrum. In the example a tungsten source is used, although the skilled person would appreciate that other materials might be appropriate.

Incident ray paths 5a to 5c are shown through the scanning zone between the x-ray source 1 and, respectively, the detectors 3a to 3c.

A suitable scanning arm 2 on which the source 1 and detector arrays 3a to 3c are mounted causes the source and linear arrays to move together relative to an object to be scanned 9 so that the object is caused to intercept the ray paths 5a to 5c in the scanning zone. A possible application of this embodiment of the invention is as a security scanner, and object 9 can be considered typically to be a container that is expected to contain a variety of distinct objects which it would be useful and desirable to characterise compositionally and to view effectively in a third dimension. However, the skilled person would readily appreciate that the same principles can be applied for example to the scanning of objects for internal examination purposes, to medical scanning, and to similar applications.

Figure 1B:
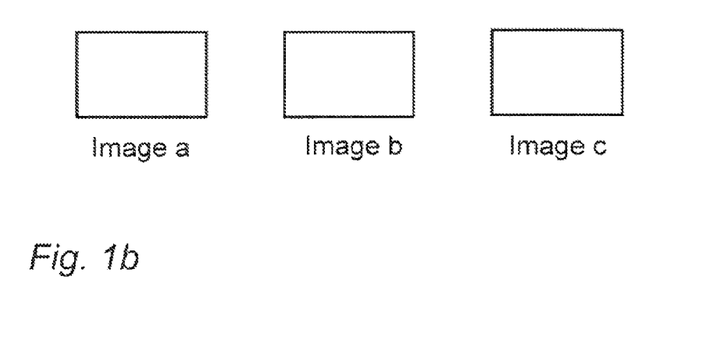

Images a to c of FIG. 1b are generated by building up transmitted information from each of the three detectors 3a to 3c. As is illustrated in FIG. 1, these generate three views, respectively identified as left, middle and right, which represent equivalent images from different ray paths (respectively 5a to 5c). These together form a single sequence of images. The geometry will cause the image sequence to roll, and display of the images successively would enable third dimensional cues to be obtained from the monocular movement parallax between them.

Figure 2:
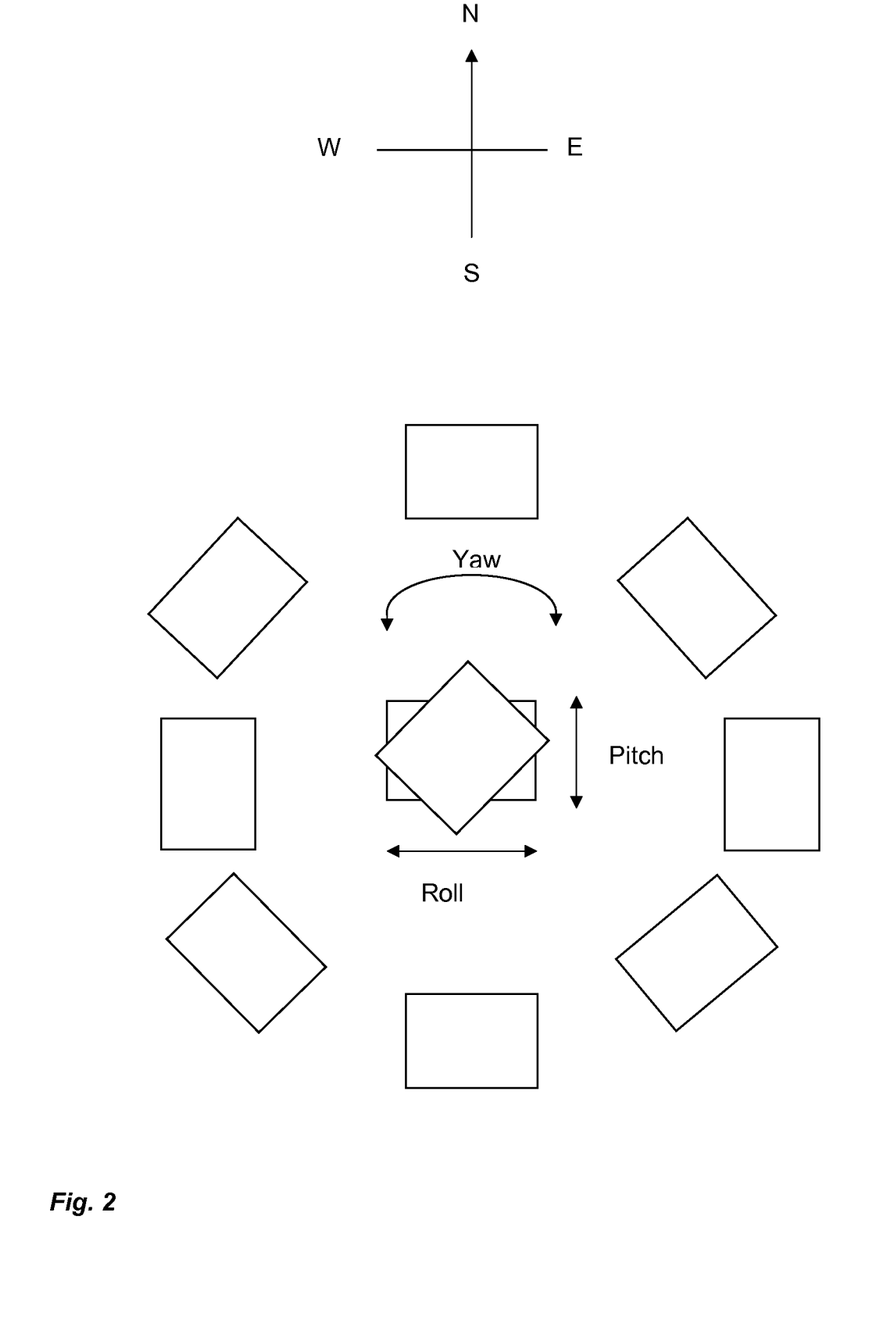
FIG. 2 illustrates the effect created by multiple series of images generated by means of the principles of FIG. 1.

FIG. 1 illustrates a single scan direction. However, the invention is distinctly characterised in having multiple scan directions at an angle to each other. This effect is illustrated in FIG. 2, which shows a representation of a plan view of image sequences produced for four scan directions, all of which pass through the common notional centre. In the illustrated example, an image sequence generated in a notional "North-South" direction gives pitch, an image sequence generated in a notional "East-West" direction gives roll, and rotation about a central axis gives yaw. Thus, an image is generated in which the monocular movement parallax effect can be used to generate more comprehensible information by animating sequential images in all three dimensions.

If the manipulated images are merely raw image radiographs generated from a series of linear array detectors from a curtain beam generated by a point source they will suffer a degree of distortion as a result of vignetting. Although, as noted above, the image is not distorted in the scan direction, the image will be distorted as a result of beam spreading in the perpendicular direction. If multiple images along multiple axes are generated this distortion will be in multiple directions. This effect is illustrated schematically in FIG. 3.

Figure 3:
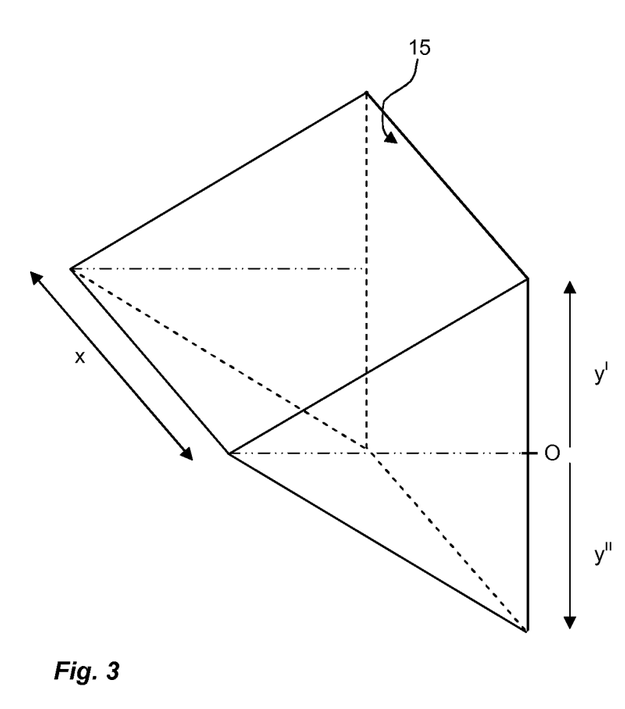
FIG. 3 illustrates distortion in uncorrected images.

Direction x in FIG. 3 is the direction of relative movement between the x-ray source and object. The image is generated in plane 15. Image distortion is in directions y' and y" with the distortion increasing with increasing distance from the centre point O.

Accordingly, in accordance with the principles of the invention, each generated image is subjected to a suitable correction to bring the image aspect ratio back to one to one, for example by applying a suitable image correction factor in the perpendicular direction so that dimensions in the scan direction and in the perpendicular direction which are equal in reality are maintained as equal in the generated image.

This makes the technique much more powerful, since images are now undistorted in both directions, and relative comprehension of different images as the monocular movement parallax effect is used fully in three dimensions is enhanced.

Figure 4:
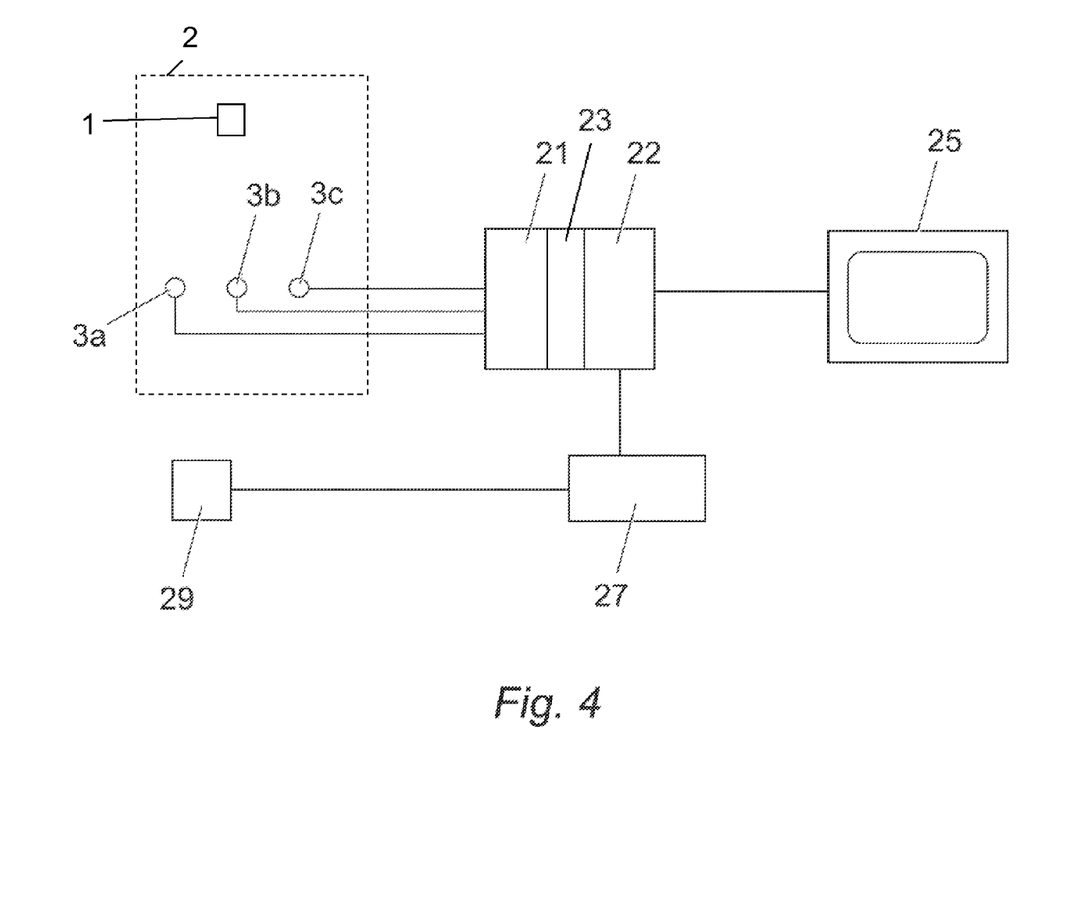
FIG. 4 is a schematic representation of an image processing and display system with image aspect ratio correction.
Figure 5:
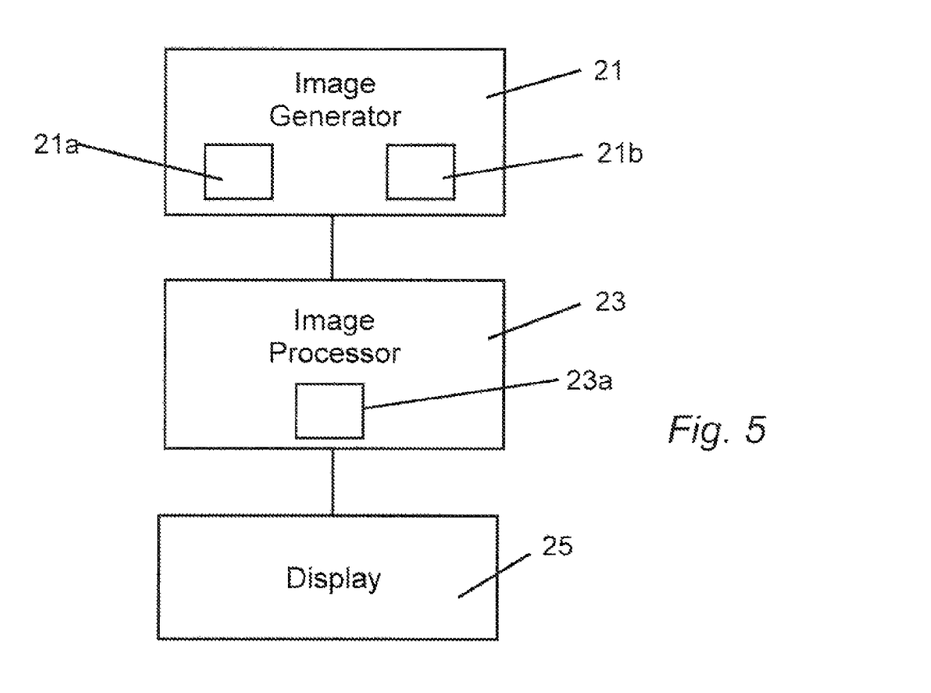
FIG. 5 is a schematic representation of an image generator and image processor according to the present invention.

A suitable apparatus by means of which images can be manipulated and displayed is represented schematically in FIG. 4.

Referring to FIG. 4, a scanning module 2 which mounts in fixed relationship a source 1 and a series of detectors 3a to 3c is used to cause relative movement of source and detectors to an object (scanning arm 2, and/or object handler 10) so that the object is caused to pass through the scanning zone.

Data is collected from the three detector arrays 3a to 3c and transmitted to a data collection and processing unit 21 which assembles and collates the data and produces individual images characteristic of the collected data from each detector. These are passed to an image storage register 22.

The key to the interpretation of the images in the manner envisaged by the invention lies in the way that the images are displayed. A simple display, 25, comprising in this example a two-dimensional video display screen is provided. Images are passed from the image register 22 to be displayed thereon successively and sequentially. The result of this successive sequential display is that an observer viewing the screen 25 is able to glean information from the successive images, and in particular third-dimensional cues, by means of monocular movement parallax between them.

If it was desirable merely to view a series of images collected along a single axis, such a simple display may be sufficient. Each image would suffer from the distortion problem set out above, but in the same sense, and this might not detract significantly from the information that an observer viewing the screen 25 would be able to obtain. However, in accordance with the invention, a successive sequence of images is collected along a plurality of axes at an angle to each other. Each successive series would have a systematic distortion in a different sense. Accordingly, it is preferable, if the images are to be interpreted successfully and to their maximum potential, that each image is first subject to a numerical correction to eliminate the distortion attributable to the beam spreading.

Accordingly, the apparatus further includes an image analysis module 23 comprising a means to apply a suitable image analysis correction 23a to the collected image data, and in particular preferably comprising a means to apply a scaling factor to image data in a direction perpendicular to a scanning direction so as to generate an image dataset for storage in the register 22 in which the aspect ratio (the ratio of apparent length in a scanning direction to apparent length perpendicular to a scanning direction) closely correlates to reality. This substantially removes the relative distortion between images in different scan directions, and means that an observer viewing the screen 25 is better able to interpret information from successive images in multiple directions.

The data collection and processing unit 21 optionally includes a direct image module 21a and an intermediate image module 21b for example in the form of suitable processing software. The direct image module generates an image dataset representing the incident information dataset at each of the three detector arrays 3a to 3c. The intermediate image module generates virtual image datasets based on numerical processing of the incident information datasets of each adjacent pair of detector arrays 3a to 3c. In the illustrated embodiment the intermediate image generator is configured to generate two or more intermediate images from each adjacent pair which show a gradual transition between the direct images produced by each adjacent pair by processing the output of the or each said pair of detectors and generating image representatives of a transition between the two said detected outputs.

In one possible embodiment a single intermediate image is generated for each collective pair. Thus the data register 22 stores five images which can be displayed sequentially. In a second possible embodiment two virtually spaced intermediate images are generated for each collective pair. Thus the data register 22 stores at least seven images which can be displayed sequentially. Other array and intermediate image protocols may be applied.

Of course, the principles of the invention are not limited to three linear detectors and are not limited to one or two intermediate images generated by each adjacent pair but apply to any series of three or more images that in effect show an object in successively varying position, and particularly preferably six or more images, especially seven or more when generated from five or fewer detectors.

Further, the software that generates the intermediate images between detector outputs can generate intermediate images between scan directions (for example, referring to FIG. 2, image position NW can be generated from N and W images or a NNW image can be generated from NW and N images). This gives the ability to rotate and manipulate the image smoothly with three degrees of freedom rather than manipulation being limited only to the scan directions with a need to come back to the centre point before tracking a different scan direction. The principle can be seen as analogous to that by which engineering models are manipulated in CAD and allows an operator viewing the object to get a better understanding of the structure of the object.

Using this interpolation would, for example, generate intermediate images around the outer circle of images shown in FIG. 2. It might be desirable to use a minimum of three scanning directions and preferably at least four, with the intermediate images generated between these directions to smooth the transition between the images.

The sequential display of images on the screen 25 is under user control by the control means 27. This allows a user to generate animated sequences from the succession of images stored in the data register 22, and effectively to manipulate the collection of images to gain significant third dimensional cues from the collected data. Optionally to further enhance this the control means 27 includes a means 29 to control the scanning arm to allow a user to manipulate the scan direction dynamically.

In the illustrated embodiment, detectors are used which are capable of resolving the transmitted x-rays spectroscopically. This resolved spectroscopic information forms part of the data that is subsequently processed to provide materials identification of the objects in the image.

In accordance with the example embodiment three linear array detectors are illustrated in series. It would be understood that even a pair of detectors would generate a pair of images from which monocular movement parallax could be obtained, and that in a practical system it might well be desirable to have a larger plurality of detectors in series. Three detectors are presented by way of illustration only. Nevertheless, an effective manipulatable and animatable image series can be obtained from a relatively small number of linear detectors in series, especially if suitable algorithms are used within the imaging system to generate intermediate images from collected data and to correct for vignetting effects.

The invention claimed is:

1. An apparatus for generating and displaying successive images of an object comprising:
   a radiation source and a series of at least two linear detectors configured to detect incident radiation spaced therefrom to define a scanning zone therebetween;
   means for causing the object to move relative to and through the scanning zone in successive passes along at least two linear directions at an angle to each other;
   a processor comprising:
      an image processing apparatus adapted to process collected image data from the output of the linear detectors in such manner as to reduce distortion attributable to beam spreading in a direction perpendicular to a scan direction; and
      an image generation apparatus configured to generate for each successive pass at least a first image from the collected image data from the output of a first linear detector of the at least two linear detectors, a second image from the collected image data from the output of a second linear detector of the at least two linear detectors, and a third image; and
   an image display configured to successively display at least the first, second and third images and thus display a monocular movement parallax between the images.

2. An apparatus in accordance with claim 1 wherein the image processing apparatus includes a correction module configured to apply a numerical image analysis to collected image data to compensate for the distortion attributable to beam spreading in a direction perpendicular to a scan direction.

3. An apparatus in accordance with claim 2 wherein the numerical image analysis is configured to apply a numerical scaling factor to a position of the collected image data in a direction perpendicular to the scan direction.

4. An apparatus in accordance with claim 1 wherein the means for causing the object to move is configured to effect relative movement of the object and the scanning zone.

5. An apparatus in accordance with claim 1 wherein the means for causing the object to move includes a means to translate the detectors and the source relative to the object, wherein the object is static, to create the relative movement.

6. An apparatus in accordance with claim 1 wherein the means for causing the object to move includes a scanning arm on which the source and the detectors are mounted for carrying the source and the detectors in fixed space relationship to each other to create a moveable scanning zone.

7. An apparatus in accordance with claim 1 wherein the linear detectors include a laterally spaced series of detectors that are mounted generally parallel to one another.

8. An apparatus in accordance with claim 1 wherein the at least two linear detectors comprise a laterally spaced series of at least three linear detectors configured to generate at least the first, second and third images for successive display.

9. An apparatus in accordance with claim 8 wherein each linear detector in the laterally spaced series comprises a linear array of photodiode cells.

10. An apparatus in accordance with claim 1 wherein the image generation apparatus includes an intermediate image generator configured to generate at least one intermediate image from at least one adjacent pair of linear detectors, by processing the output of said pair of detectors and generating an image representative of an output intermediate between the two said detected outputs.

11. An apparatus in accordance with claim 1 wherein the image generation apparatus includes an intermediate image generator configured to generate at least one intermediate image from at least one pair of image positions respectively generated at first and second pass directions, by processing the detected output for each such image position and generating an image representative of an output intermediate between the two said detected outputs.

12. An apparatus in accordance with claim 1 wherein at least some of the linear detectors comprise detectors that are configured to generate spectroscopic information about the incident radiation by exhibiting a spectroscopically variable response across at least a substantial part of a source spectrum allowing spectroscopic information to be retrieved.

13. An apparatus in accordance with claim 12 including an image processing means configured to represent spectroscopic resolution of the source spectrum in a generated image.

14. An apparatus in accordance with claim 12 wherein the at least some detectors are configured to exhibit a direct spectroscopic response in that it is fabricated from a semiconductor material selected to exhibit inherently as a direct material property a direct variable electrical and photoelectric response to different parts of the source spectrum.

15. An apparatus in accordance with claim 14 wherein the semiconductor material is selected from cadmium telluride, cadmium zinc telluride (CZT), cadmium manganese telluride (CMT), germanium, lanthanum bromide, and thorium bromide.

16. An apparatus in accordance with claim 14 wherein the semiconductor material comprises crystalline $Cd_{1-(a+b)}Mn_aZn_b Te$ where $a+b<1$ and a and/or b may be zero.

17. A method of obtaining successive images of an object comprising the steps of:
   providing a radiation source and a series of at least two linear detectors configured to detect incident radiation spaced therefrom to define a scanning zone therebetween, the at least two linear detectors including a first linear detector and a second linear detector;
   causing the object to move relative to and through the scanning zone in successive passes in at least two linear directions at an angle to each other;
   generating for each successive pass at least a first image from the collected image data from the output of the first linear detector, at least a second image from the collected image data from the output of the second linear detector; and at least one third image;
   processing collected image data for each image in such manner as to reduce distortion attributable to beam spreading in a direction perpendicular to a scan direction; and
   displaying at least the first, second and third images successively and thus displaying a monocular movement parallax between the images.

18. A method in accordance with claim 17 wherein the step of processing the collected image data for each image comprises applying a numerical image analysis to the collected data to compensate for the distortion attributable to beam spreading in a direction perpendicular to a scan direction.

19. A method in accordance with claim 18 wherein the numerical image analysis comprises applying a numerical scaling factor to a notional position of the collected data in a direction perpendicular to the scan direction.

20. A method in accordance with claim 17 wherein the step of causing the object to move involves moving the detectors and the source in fixed relationship to each other and relative to the object, wherein the object is static, to create the relative movement.

21. A method in accordance with claim 17 wherein the at least two linear detectors comprise a laterally spaced series of at least three linear detectors that are configured to generate at least the first, second and third images for successive display.

22. A method in accordance with claim 17 additionally comprising generating at least one intermediate image from at least one adjacent pair of the linear detectors, by processing the output of said pair of detectors and generating an image representative of an output intermediate between the two said detected outputs.

23. A method in accordance with claim 17 additionally comprising generating at least one intermediate image from at least one pair of image positions respectively generated during first and second pass directions, by processing the detected output for each such image position and generating an image representative of an output intermediate between the two said detected outputs.

24. A method in accordance with claim 17 wherein multiple images from the successive passes are combined and presented successively in a manner which allows manipulation of the object axis around which the object is being viewed in three dimensions.

25. A method in accordance with claim 17 wherein images generated by at least some of the at least two linear detectors are resolved spectroscopically across at least a substantial part of a source spectrum, and spectroscopic resolution obtained from the output of each such linear detector is represented in a displayed image.

26. A method of obtaining imaging data from a part of a human or animal body comprising scanning the part of the body as an object in accordance with claim 17.

27. A method of diagnosis of a disorder of a human or animal body including the step of imaging the body in accordance with claim 26, and the further step of evaluating an image to identify a disorder state.

* * * * *

UNITED STATES PATENT AND TRADEMARK OFFICE
CERTIFICATE OF CORRECTION

PATENT NO. : 8,660,237 B2  Page 1 of 1
APPLICATION NO. : 13/148621
DATED : February 25, 2014
INVENTOR(S) : Max Robinson It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 120 days.

Signed and Sealed this

Twenty-ninth Day of September, 2015

Michelle K. Lee
*Director of the United States Patent and Trademark Office*